United States Patent [19]
Kato et al.

[11] Patent Number: 6,045,822
[45] Date of Patent: Apr. 4, 2000

[54] LIPOSOME PREPARATIONS OF INDOLOCARBAZOLE DERIVATIVES DESCRIPTION

[75] Inventors: Yasuki Kato; Masahiro Yamauchi; Kunio Ito, all of Shizuoka, Japan

[73] Assignee: Kyowa Hakko Kogyo Co., Ltd., Tokyo, Japan

[21] Appl. No.: 09/025,752

[22] Filed: Feb. 18, 1998

Related U.S. Application Data

[63] Continuation-in-part of application No. PCT/JP97/02033, Jun. 12, 1997.

[30] Foreign Application Priority Data

Jun. 18, 1996 [JP] Japan ..................................... 8-156459

[51] Int. Cl.$^7$ ................................................. A61K 9/127
[52] U.S. Cl. ........................................... 424/450; 514/211
[58] Field of Search .............................. 424/450; 514/211

[56] References Cited

U.S. PATENT DOCUMENTS

| | | | |
|---|---|---|---|
| 4,952,567 | 8/1990 | DeMeyts | 514/54 |
| 5,344,924 | 9/1994 | Murakala | 540/545 |
| 5,658,898 | 8/1997 | Weder | 514/211 |

FOREIGN PATENT DOCUMENTS

| | | |
|---|---|---|
| 0383919 | 8/1990 | European Pat. Off. . |
| 3-163031 | 7/1991 | Japan . |
| 7-278016 | 10/1995 | Japan . |
| WO 07105 | 8/1989 | WIPO . |

OTHER PUBLICATIONS

Tschaikowsky in BBA 1222 p 113–121, 1994.
The Journal of Antibiotics, vol. XL, No. 12 (1987) 1782–84.
Cancer Research, vol. 51 (Sep. 1991) 4888–92.

*Primary Examiner*—Gollamudi S. Kishore
*Attorney, Agent, or Firm*—Fitzpatrick, Cella, Harper & Scinto

[57] ABSTRACT

The present inventions provides a liposome preparation characterized by encapsulating indolocarbazole derivatives represented by formula (I):

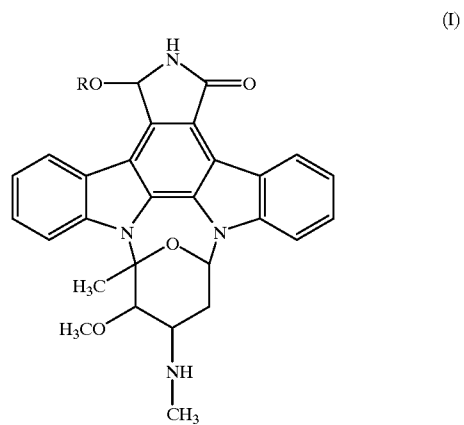

(I)

(wherein R represents hydrogen or lower alkyl) into a liposome comprising lipids.

2 Claims, 1 Drawing Sheet

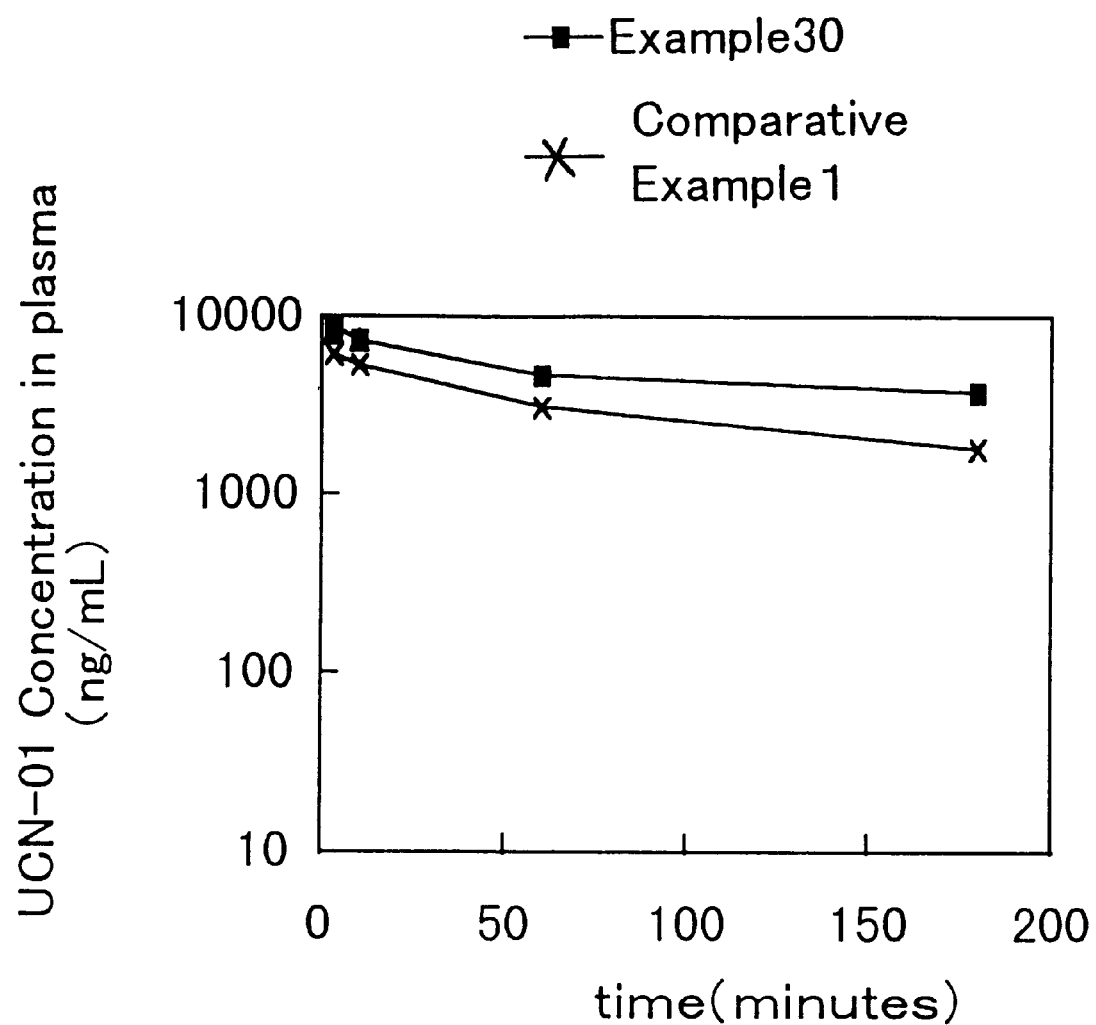

LIPOSOME PREPARATIONS OF INDOLOCARBAZOLE DERIVATIVES

DESCRIPTION

CROSS REFERENCE TO RELATED APPLICATION

This application is a continuation-in-part of PCT Patent Application No. PCT/JP 97/02033, filed Jun. 12, 1997.

TECHNICAL FIELD

The present invention relates to a liposome preparation containing a medically useful indolocarbazole derivative.

BACKGROUND ART

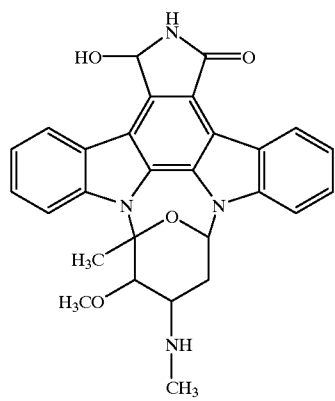

UCN-01

It is known that UCN-01 has protein kinase C inhibitory activity [J. Antibiotics., 40, 1782 (1987)] and has anti-tumor activity [Cancer Res., 51, 4888 (1991)]. Further, it is disclosed in WO89/07105 that the UCN-01 derivative possesses inhibitory activity on cell growth.

In case UCN-01 or its derivative is administered in vivo particularly to blood vessels, it would be impossible to prevent UCN-01 or its derivative from contacting vascular cells and other various normal cells, as well. Because the UCN-01 derivative has inhibitory activity on cell growth, the contact of UCN-01 or its derivative with normal cells may cause certain adverse effects on normal cells.

In case UCN-01 or its derivative is administered as such to blood vessels, the compound may undergo decomposition in blood or be accumulated in internal organs other than the target, and is thus not necessarily accumulated in tumors effectively Also, the compound may bind thightly onto the serum components before accumulation in the target turmors.

There is demand for a preparation containing UCN-01 or its derivative, which is stabilized in blood and accumulated at high levels in tumors without causing any effect on normal cells.

DISCLOSURE OF THE INVENTION

The present invention relates to a liposome preparation characterized by encapsulating indolocarbazole derivatives represented by formula (I):

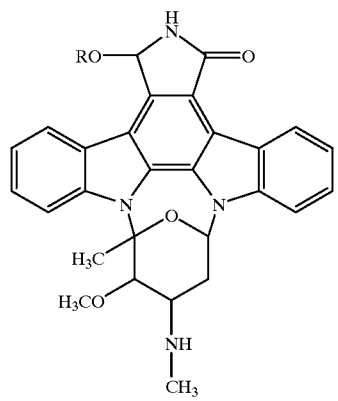

(I)

(wherein R represents hydrogen or lower alkyl) into a liposome comprising lipids.

Hereinafter, the compound represented by formula (I) is referred to as Compound (I).

In the definition for the formula of Compound (I), the lower alkyl refers to straight chain or branched chain of C1 to C6 alkyl, for example, methyl, ethyl, propyl, isopropyl, sec-butyl, tert-butyl, pentyl, hexyl, etc.

The indolocarbazole derivatives represented by formula (I) can be produced by the method described in U.S. Pat. No. 4,935,415 A or EP 383919 A. Specific examples of such compounds are shown in Table 1.

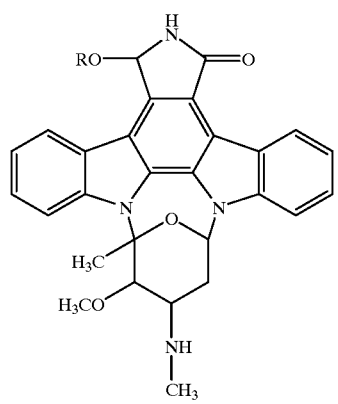

(I)

TABLE 1

Examples of compounds represented by formula (I)

| R | Molecular Weight:MS (m/z) |
|---|---|
| H | 483 $(M + 1)^+$ |
| $CH_3$ | 497 $(M + 1)^+$ |
| $C_2H_5$ | 510 $(M)^+$ |
| $i-C_3H_7$ | 524 $(M)^+$ |
| $n-CH_4H_9$ | 538 $(M)^+$ |

As the lipids for preparation of liposomes, mention is made of phospholipids, glyceroglycolipids, and sphingoglycolipids among which phospholipids are preferably used. Examples of such phospholipids include natural or synthetic phospholipids such as phosphatidylcholine, phosphatidylethanolamine, phosphatidylserine, phosphatidic acid, phosphatidylglycerol, phosphatidylinositol, lysophosphatidylcholine, sphingomyelin, egg yolk lecithin and soybean lecithin, as well as hydrogenated phospholipids etc.

The glyceroglycolipids include sulfoxyribosyldiglyceride, diglycosyldiglyceride, digalactosyldiglyceride, galactosyldiglyceride, glycosyldiglyceride, etc.

The sphingoglycolipids include galactosylcerebroside, lactosylserebroside, ganglioside etc. These are used singly or in combination. If necessary, sterols such as cholesterol as membrane stabilizer, tocopherol, etc. as antioxidant, stearylamine, dicetylphosphate, ganglioside, etc. as charged substances, may be used in addition to the lipid component.

Modification of the surfaces of liposomes with a non-ionic surface active agent, cationic surface active agent, anionic surface active agent, polysaccharides and derivatives thereof, polyoxyethylene derivatives etc. can be carried out arbitrarily. Further modification of the surfaces of liposomes with antibodies, proteins, peptides, aliphatic acids etc. can be applied for the purpose of targeting. The solution used for suspending liposomes may be an acid, alkali, various buffers, physiological saline, amino acid infusions etc. in addition to water. Further, antioxidants such as citric acid, ascorbic acid, cysteine, ethylenediaminetetraacetic acid (EDTA) etc. may also be added. Furthermore, preservatives such as paraben, chlorobutanol, benzyl alcohol, propylene glycol etc. may also be added. In addition, glycerin, glucose, sodium chloride etc. can also be added as agents for rendering the solution isotonic.

For production of the liposome preparation of the present invention, a method of preparing a known liposome preparation can be used. The known method of preparing a liposome preparation includes the liposome preparation method of Bangham et al. (J. Mol. Biol., 13, 238 (1965)), the ethanol injection method (J. Cell. Biol., 66, 621 (1975)), the French press method (FEBS Lett., 99, 210 (1979)), the freezing and thawing method (Arch. Biochem. Biophys., 212, 186 (1981)), the reverse phase evaporation method (Proc. Natl. Acad. Sci. (USA), 75, 4194 (1978)), and the pH gradient method (Biochim. Biophys. Acta, 816, 294 (1985); Japanese Patent Application Laid-Open Publication No. 165,560/95).

Among these methods, the pH gradient method has a large number of advantages including, for example, high encapsulation efficiency of Compound (I) in the liposome, the uniform size of the resulting liposomes, a smaller amount of the remaining organic solvent in the liposome suspension. The method of preparing the liposome preparation of the present invention by use of the pH gradient method is as follows: For example, the lipids are dissolved in a solvent such as ether, ethanol etc. and then placed in an round-bottomed flask, and the solvent is evaporated to form a lipid film. Then, an acidic buffer is added to the film, followed by shaking and stirring to form larger multilamellar liposomes. The liposome particles are prepared by the extrusion method etc. so that their average particle diameter is made e.g. about 100 nm. After a weakly acidic solution of Compound (I) is added to this liposome suspension, a suitable buffer is added so that the pH of the liposome suspension is raised at about neutrality (the difference between the pH values of the liposome suspension before and after the rise of pH is preferably 3 or more). By the above operation, Compound (I) can be encapsulated in the inside of the liposomes.

Alternatively, liposomes can also be formed by dissolving Compound (I) and the lipid component in organic solvent such as ethanol etc., then evaporating the solvent off, and adding physiological saline thereto followed by shaking and stirring.

The liposome preparation of the present invention obtained by e.g. the methods described above can be used as such, but can also be lyophilized after adding fillers such as mannitol, lactose, glycine etc. depending on the object of use, storage conditions etc. Lyoprotectants stabilizers such as glycerin etc. may also be added before lyophilization.

The liposome preparation of the present invention is used generally as an injection, but can also be used as an oral dosage form, nasal dosage form, eye drop, percutaneous dosage form, suppository, inhalation etc. by manufacturing the preparation into such forms.

Hereinafter, the Examples and Test Examples of the present invention are shown.

The object of the liposome preparation of the present invention is to stabilize Compound (I) in blood and to increase its accumulation in tumors.

BRIEF OF DESCRIPTION THE DRAWING

FIG. 1 shows the change of UCN-01 concentration in the plasma of a rat with the elapse of time.

BEST MODE FOR CARRYING OUT THE INVENTION

EXAMPLE 1 phosphatidylcholine 0.7 g was dissolved in 5 ml ether, and the solvent was evaporated under reduced pressure to form a lipid film. 10 ml of 20 mM citrate buffer, pH 2.5 was added to it and shaken and stirred with a Vortex mixer. Further, this suspension was passed 5 times through 0.4 µm polycarbonate membrane filter. Further, the filtrate was passed 10 times through 0.1 µm polycarbonate membrane filter. A 20 mM citrate buffer, pH 2.5 was added to it to prepare a liposome suspension containing 50 mg/ml phosphatidylcholine. Separately, 200 mg lactose, 56 mg $Na_2HPO_4.12 H_2O$ and 12 mg hydrous citric acid were added to 10 mg UCN-01, and the mixture was dissolved in a distilled water to give 10 ml solution which was then introduced into a glass vial and lyophilized. After lyophilization, the glass vial was returned to normal pressure under a nitrogen stream and sealed to give a lyophilized product of UCN-01 in it. To this lyophilized product was added 2 ml of the previously prepared liposome suspension. Further, 8 ml of 200 mM $Na_2HPO_4$ solution disodium phosphate was added thereto to adjust the pH to 7.4 so that UCN-01 was encapsulated in liposomes.

EXAMPLE 2

A liposome suspension was prepared in the same manner as in Example 1 except that the concentration of phosphatidylcholine was made 40 mg/ml by changing the amount of 20 mM citrate buffer, pH 2.5. Separately, 200 mg of lactose, 56 mg of $Na_2HPO_4.12 H_2O$, and 12 mg of hydrous citric acid were added to 10 mg UCN-01, and a lyophilized product was prepared in the same manner as in Example 1. To this lyophilized product was added 2 ml of the previously prepared liposome suspension. Further, 8 ml of 200 mM $Na_2HPO_4$ solution was added thereto to adjust the pH to 7.4 so that UCN-01 was encapsulated in liposomes.

EXAMPLE 3

A liposome suspension was prepared in the same manner as in Example 1 except that the concentration of phosphatidylcholine was made 30 mg/ml by changing the amount of 20 mM citrate buffer, pH 2.5. Separately, 200 mg of lactose, 56 mg of $Na_2HPO_4.12 H_2O$, and 12 mg of hydrous citric acid were added to 10 mg UCN-01, and a lyophilized product was prepared in the same manner as in Example 1. To this lyophilized product was added 2 ml of the previously prepared liposome suspension. Further, 8 ml of 200 mM $Na_2HPO_4$ solution was added thereto to adjust the pH to 7.4 so that UCN-01 was encapsulated in liposomes.

EXAMPLE 4

A liposome suspension was prepared in the same manner as in Example 1 except that the concentration of phosphatidylcholine was made 25 mg/ml by changing the amount of 20 mM citrate buffer, pH 2.5. Separately, 200 mg of lactose, 56 mg of $Na_2HPO_4.12\ H_2O$, and 12 mg of hydrous citric acid were added to 10 mg UCN-01, and a lyophilized product was prepared in the same manner as in Example 1. To this lyophilized product was added 2 ml of the previously prepared liposome suspension. Further, 8 ml of 200 mM $Na_2HPO_4$ solution was added thereto to adjust the pH to 7.4 so that UCN-01 was encapsulated in liposomes.

EXAMPLE 5

A liposome suspension was prepared in the same manner as in Example 1 except that the concentration of phosphatidylcholine was made 25 mg/ml by changing the amount of 20 mM citrate buffer, pH 2.5. 5 mg UCN-01 was dissolved by adding 2 ml of the prepared liposome suspension. Further, 3 ml of 200 mM $Na_2HPO_4$ solution was added thereto to adjust the pH to 7.4 so that UCN-01 was encapsulated in liposomes.

EXAMPLE 6

A liposome suspension was prepared in the same manner as in Example 1 except that the concentration of phosphatidylcholine was made 20 mg/ml by changing the amount of 20 mM citrate buffer, pH 2.5. 5 mg UCN-01 was dissolved by adding 2 ml of the prepared liposome suspension. Further, 3 ml of 200 mM $Na_2HPO_4$ solution was added thereto to adjust the pH to 7.4 so that UCN-01 was encapsulated in liposomes.

EXAMPLE 7

A liposome suspension was prepared in the same manner as in Example 1 except that the concentration of phosphatidylcholine was made 15 mg/ml by changing the amount of 20 mM citrate buffer, pH 2.5. 5 mg UCN-01 was dissolved by adding 2 ml of the prepared liposome suspension. Further, 3 ml of 200 mM $Na_2HPO_4$ solution was added thereto to adjust the pH to 7.4 so that UCN-01 was encapsulated in liposomes.

EXAMPLE 8

A liposome suspension was prepared in the same manner as in Example 1 except that the concentration of phosphatidylcholine was made 12.5 mg/ml by changing the amount of 20 mM citrate buffer, pH 2.5. 5 mg UCN-01 was dissolved by adding 2 ml of the prepared liposome suspension. Further, 3 ml of 200 mM $Na_2HPO_4$ solution was added thereto to adjust the pH to 7.4 so that UCN-01 was encapsulated in liposomes.

EXAMPLE 9

5 mg UCN-01 and 100 mg phosphatidylcholine were dissolved in 15 ml ethanol. The solvent was evaporated under reduced pressure whereby a lipid film was formed. 1 ml of 5 weight-% glucose was added thereto and shaken and stirred with a Vortex mixer. This liposome suspension was passed 4 times through 0.4 µm polycarbonate membrane filter. Further, the filtrate was passed 10 times through 0.1 µm polycarbonate membrane filter so that UCN-01 was encapsulated in liposomes.

Test Example 1

Each of the UCN-01 encapsulating liposomes prepared in Examples 1 to 8 was filtered through 0.45 µm membrane filter to remove insolubles etc. In the case of the liposomes of Examples 1 to 4, 1 ml of 200 mM disodium phosphate-20 mM citrate buffer, pH 7.4 was added there and the mixtures was mixed with 1 ml of liposome suspension. These liposomes were ultracentrifuged (110,000×g, 1 hour) at 10° C. The phospholipid before and after filtration, and the phospholipid in the supernatant after ultracentrifugation, were quantified by the enzyme method [Practical Clinical Chemistry (enlarged edition), 580 (1982)] using Determiner PL (KYOWA MEDEX CO., LTD.). In addition, UCN-01 before and after filtration, and UCN-01 in the supernatant after ultracentrifugation, were quantified by high performance liquid chromatography. The encapsulation efficiency was calculated by the following formula.

Encapsulation efficiency $(\%)=[(A-B)/(C-D)]/(E/F)\times100$

A: Concentration of UCN-01 in the filtrate after filtration (mg/ml)

B: Concentration of UCN-01 in the supernatant after ultracentrifugation (mg/ml)

C: Concentration of the phospholipid in the filtrate after filtration (mg/ml)

D: Concentration of the phospholipid in the ultracentrifuged supernatant (mg/ml)

E: Concentration of UCN-01 in the suspension before filtration (mg/ml)

F: Concentration of the phospholipid in the suspension before filtration (mg/ml)

Analytical Conditions for High Performance Liquid Chromatography

Column: Capsule pack PAK C18 UG120 (SHISEID Co., Ltd.) S-5, 4.6 mm×250 mm
Mobile phase: 20 mM Tris-HCl buffer, pH 9.0: acetonitrile:tetrahydrofuran=60:22:18 (parts by volume).
Flow rate: 0.8 ml/min.
Column temperature: 25° C.
Detection wavelength: 285 nm.

The results are shown in Table 2.

TABLE 2

| Sample | Encapsulation efficiency of UCN-01 (%) |
|---|---|
| Encapsulation efficiency of UCN-01 | |
| Example 1 | 108.3 |
| Example 2 | 98.1 |
| Example 3 | 81.8 |
| Example 4 | 68.4 |
| Example 5 | 101.6 |
| Example 6 | 91.8 |
| Example 7 | 78.7 |
| Example 8 | 56.8 |

Test Example 2

To determine the leakage of UCN-01 from liposomes, a UCN-01 encapsulating liposome suspension prepared in the same manner as in Example 1 was introduced into a vial and sealed with a rubber stopper. Obtained samples were stored at different temperatures of 5° C., 25° C., and 37° C., respectively, and the change with time of encapsulation efficiency of UCN-01 was determined. The method of determining the encapsulation efficiency was carried out in the same manner as in Test Example 1.

The results are shown in Table 3.

TABLE 3

Change with Time of Encapsulation
efficiency of Inclusion of UCN-01

| Time | Encapsulation efficiency (%) | | |
|---|---|---|---|
| | 5° C. | 25° C. | 37° C. |
| 0 | 108.2 | 108.2 | 108.2 |
| 1 | 93.0 | 99.3 | 102.8 |
| 3 | 114.9 | 96.2 | 101.5 |
| 6 | 99.2 | 95.1 | 100.8 |
| 24 | 93.2 | 96.5 | 88.6 |

As can be seen from Table 2, the liposome preparations of the present invention indicate high encapsulation efficiency of UCN-01. In addition, Table 3 shows that the liposome preparations of the present invention are stable liposome preparations with less leakage of UCN-01.

EXAMPLE 10

1 g phosphatidylcholine was dissolved in 5 ml ether, and the solvent was evaporated under reduced pressure to form a lipid film. 10 ml of 20 mM citrate buffer, pH 4.0 was added thereto and shaken and stirred with a Vortex mixer. Further, this suspension was passed 5 times through 0.4 $\mu$m polycarbonate membrane filter. Further, the filtrate was passed 10 times through 0.1 $\mu$m polycarbonate membrane filter. A 20 mM citrate buffer, pH 4.0 was added thereto to prepare a liposome suspension containing 50 mg/ml phosphatidylcholine. Separately, 200 mg lactose, 56 mg $Na_2HPO_4.12\ H_2O$ and 12 mg hydrous citric acid were added to 10 mg UCN-01, and its lyophilized product was prepared in the same manner as in Example 1. To this lyophilized product was added 2 ml of the previously prepared liposome suspension. Further, 8 ml of 28.2 mM aqueous sodium hydroxide was added thereto to adjust the pH to 8.0 so that UCN-01 was included in liposomes.

EXAMPLE 11

UCN-01 was encapsulated in liposomes in the same manner as in Example 10 except that 1.2 g phosphatidylcholine and 0.3 g cholesterol were used as the starting materials of the lipid film.

EXAMPLE 12

UCN-01 was encapsulated in liposomes in the same manner as in Example 10 except that 1.2 g phosphatidylcholine, 0.4 g cholesterol and 0.4 g PEG-DSPE (1,2-distearoyl-sn-glycero-3-phosphoethanolamine-N-[poly-(ethyleneglycol) 2000]; a product of AVANTI POLAR LIPIDS INCORPORATION)) were used as the starting materials of the lipid film.

EXAMPLE 13

A liposome suspension was prepared in the same manner as in Example 10 except that the concentration of phosphatidylcholine in the liposome suspension was made 35 mg/ml by changing the amount of 20 mM citrate buffer, pH 4.0. Separately, a lyophilized product of UCN-01 was prepared in the same manner as in Example 10. To this lyophilized product was added the previously prepared liposome suspension so that UCN-01 was made 0.5 mg/ml. A 8 ml of 10.4 mM aqueous sodium hydroxide was added to 2 ml of this solution to adjust the pH to 8.0 so that UCN-01 was encapsulated in liposomes.

EXAMPLE 14

A liposome suspension and a lyophilized product of UCN-01 were prepared in the same manner as in Example 13. The liposome suspension was added to this lyophilized product so that UCN-01 was made 0.05 mg/ml. A 8 ml of 9.0 mM aqueous sodium hydroxide was added to 2 ml of this solution to adjust the pH to 8.0 so that UCN-01 was encapsulated in liposomes.

EXAMPLE 15

A liposome suspension and a lyophilized product of UCN-01 were prepared in the same manner as in Example 13. The liposome suspension was added to this lyophilized product so that UCN-01 was made 0.005 mg/ml. A 8 ml of 9.0 mM aqueous sodium hydroxide was added to 2 ml of this solution to adjust the pH to 8.0 so that UCN-01 was encapsulated in liposomes.

EXAMPLE 16

UCN-01 was encapsulated in liposomes in the same manner as in Example 13 except that 0.2 $\mu$m polycarbonate membrane filter was used in place of the 0.1 $\mu$m polycarbonate membrane filter to prepare a liposome suspension.

EXAMPLE 17

A liposome suspension and a lyophilized product of UCN-01 were prepared in the same manner as in Example 16. The liposome suspension was added to this lyophilized product so that UCN-01 was made 0.05 mg/ml. A 8 ml of 9.0 mM aqueous sodium hydroxide was added to 2 ml of this solution to adjust the pH to 8.0 so that UCN-01 was encapsulated in liposomes.

EXAMPLE 18

A liposome suspension and a lyophilized product of UCN-01 were prepared in the same manner as in Example 16. The liposome suspension was added to this lyophilized product so that UCN-01 was made 0.005 mg/ml. A 8 ml of 9.0 mM aqueous sodium was added to 2 ml of this solution to adjust the pH to 8.0 so that UCN-01 was encapsulated in liposomes.

EXAMPLE 19

0.9 g phosphatidylcholine and 0.1 g phosphatidylethanolamine were evaporated in 5 ml chloroform, and the solvent was evaporated under reduced pressure whereby a lipid film was formed. 10 ml of 20 mM citrate buffer, pH 4.0 was added thereto and shaken and stirred with a Vortex mixer. This suspension was passed 5 times through 0.4 $\mu$m polycarbonate membrane filter. Further, the filtrate was passed 10 times through 0.1 $\mu$m polycarbonate membrane filter. 20 mM citrate buffer, pH 4.0 was added thereto to prepare a liposome suspension containing 45 mg/ml phosphatidylcholine. Separately, a lyophilized product of UCN-01 was prepared in the same manner as in Example 10. To this lyophilized product was added the previously prepared liposome suspension so that UCN-01 was made 0.5 mg/ml. A 8 ml of 10.4 mM aqueous sodium hydroxide was added to 2 ml of this solution to adjust the pH to 8.0 so that UCN-01 was encapsulated in liposomes.

EXAMPLE 20

A liposome suspension and a lyophilized product of UCN-01 were prepared in the same manner as in Example 19. The liposome suspension was added to this lyophilized product so that UCN-01 was made 0.05 mg/ml. A 8 ml of 9.0 mM aqueous sodium hydroxide was added to 2 ml of this solution to adjust the pH to 8.0 so that UCN-01 was encapsulated in liposomes.

EXAMPLE 21

A liposome suspension and a lyophilized product of UCN-01 were prepared in the same manner as in Example 19. The liposome suspension was added to this lyophilized product so that UCN-01 was made 0.005 mg/ml. A 8 ml of 9.0 mM aqueous sodium hydroxide was added to 2 ml of this solution to adjust the pH to 8.0 so that UCN-01 was encapsulated in liposomes.

EXAMPLE 22

0.7 g phosphatidylcholine and 0.3 g phosphatidylglycerol were dissolved in 5 ml chloroform, and the solvent was evaporated under reduced pressure whereby a lipid film was formed. 10 ml of 20 mM citrate buffer, pH 4.0 was added thereto and shaken and stirred with a Vortex mixer. This suspension was passed 5 times through 0.4 μm polycarbonate membrane filter. Further, the filtrate was passed 10 times through 0.1 μm polycarbonate membrane filter. A 20 mM citrate buffer, pH 4.0 was added thereto to prepare a liposome suspension containing 35 mg/ml phosphatidylcholine. Separately, a lyophilized product of UCN-01 was prepared in the same manner as in Example 10. To this lyophilized product was added the previously prepared liposome suspension so that UCN-01 was made 0.5 mg/ml. 8 ml of 10.4 mM aqueous sodium hydroxide was added to 2 ml of this solution to adjust the pH to 8.0 so that UCN-01 was encapsulated in liposomes.

EXAMPLE 23

A liposome suspension and a lyophilized product of UCN-01 were prepared in the same manner as in Example 22. The liposome suspension was added to this lyophilized product such that UCN-01 was made 0.05 mg/ml. A 8 ml of 9.0 nM aqueous sodium hydroxide was added to 2 ml of this solution to adjust the pH to 8.0 so that UCN-01 was encapsulated in liposomes.

EXAMPLE 24

A liposome suspension and a lyophilized product of UCN-01 were prepared in the same manner as in Example 22. The liposome suspension was added to this lyophilized product so that UCN-01 was made 0.005 mg/ml. A 8 ml of 9.0 mM aqueous sodium hydroxide was added to 2 ml of this solution to adjust the pH to 8.0 so that UCN-01 was encapsulated in liposomes.

EXAMPLE 25

UCN-01 was encapsulated in liposomes in the same manner as in Example 22 except that 0.7 g phosphatidylcholine and 0.3 g cholesterol were used as the starting materials of the lipid film.

EXAMPLE 26

A liposome suspension and a lyophilized product of UCN-01 were prepared in the same manner as in Example 25. The liposome suspension was added to this lyophilized product so that UCN-01 was made 0.05 mg/ml. A 8 ml of 9.0 mM aqueous sodium hydroxide was added to 2 ml of this solution to adjust the pH to 8.0 so that UCN-01 was encapsulated in liposomes.

EXAMPLE 27

A liposome suspension and a lyophilized product of UCN-01 were prepared in the same manner as in Example 25. The liposome suspension was added to this lyophilized product so that UCN-01 was made 0.005 mg/ml. A 8 ml of 9.0 mM aqueous sodium hydroxide was added to 2 ml of this solution to adjust the pH to 8.0 so that UCN-01 was encapsulated in liposomes.

Test Example 3

The UCN-01 encapsulating liposomes prepared in Examples 10 to 12 were treated in the same manner as in Test Example 1 and the encapsulation efficiency of UCN-01 in each liposome was examined. The results are shown in Table 4.

TABLE 4

Encapsulation efficiency of UCN-01 (%)

| Sample | Encapsulation efficiency of UCN-01 (%) |
|---|---|
| Example 10 | 100.0 |
| Example 11 | 85.7 |
| Example 12 | 82.9 |

Test Example 4

The UCN-01 encapsulating liposomes prepared in Examples 13 to 27 were ultracentrifuged (110,000×g, 2 hours) at 10° C. UCN-01 before ultracentrifugation, and UCN-01 in the supernatant after ultracentrifugation, were quantified by high performance liquid chromatography. The encapsulation efficiency was calculated by the following formula:

Encapsulation efficiency of UCN-01 (%)=(B−A)×100/B

A: Concentration of UCN-01 in the ultracentrifuged supernatant (mg/ml)
B: Concentration of UCN-01 in the suspension before ultracentrifugation (mg/ml)

Analytical Conditions for Hiqh Performance Liquid Chromatography
Column: YMC AM-312, 6.00 mm diameter×150 mm length manufactured by YMC Co., Ltd.).
Mobile phase: 0.05 M phosphate buffer (plus 0.1% triethylamine),
pH 7.3: acetonitrile=1:1 (part by volume).
Flow rate: 1.0 ml/min.
Column temperature: 25° C.
Detection: Excitation wavelength 310 nm, Emission wavelength 410 nm.

The results are shown in Table 5.

TABLE 5

Encapsulation efficiency of UCN-01

| Sample | Encapsulation efficiency of UCN-01 (%) |
|---|---|
| Example 13 | 98.7 |
| Example 14 | 99.0 |
| Example 15 | 96.8 |
| Example 16 | 99.2 |
| Example 17 | 99.2 |
| Example 18 | 94.0 |
| Example 19 | 99.9 |
| Example 20 | 99.7 |
| Example 21 | 88.5 |
| Example 22 | 98.9 |
| Example 23 | 99.4 |
| Example 24 | 100.0 |
| Example 25 | 99.6 |
| Example 26 | 99.4 |
| Example 27 | 92.0 |

EXAMPLE 28

1 g hydrogenated soybean lecithin was dissolved in 5 ml chloroform and the solvent was evaporated under reduced pressure whereby a lipid film was formed. 10 ml of 20 mM citrate buffer, pH 4.0 was added thereto and shaken and stirred with a Vortex mixer. The suspension was passed 5 times through 0.4 μm polycarbonate membrane filter. Further, the filtrate was passed 10 times through 0.2 μm polycarbonate membrane filter. A 20 mM citrate buffer was added thereto prepare a liposome suspension containing 50 mg/ml phosphatidylcholine. Separately, 200 mg lactose, 56 mg $Na_2HPO_4.12 H_2O$ and 12 mg hydrous citric acid were added to 10 mg UCN-01, and the mixture was dissolved in distilled water to give 10 ml solution which was then introduced into a glass vial and lyophilized. After lyophilization, the glass vial was returned to normal pressure under a nitrogen stream and sealed to give a lyophilized product of UCN-01 in it. To the lyophilized product was added 2 ml of the previously prepared liposome suspension. A 0.1 ml aliquot was removed from it followed by addition of 0.9 ml of the liposome suspension. Further, 4 ml of 10.4 mM aqueous sodium hydroxide was added thereto and left at 70° C. for 10 minutes so that UCN-01 was encapsulated in liposomes.

EXAMPLE 29

10 ml of 20 mM citrate buffer, pH 4.0 was added to 1 g hydrogenated soybean lecithin and the mixture was shaken and stirred with a Vortex mixer. The suspension was passed 5 times through 0.4 μm polycarbonate membrane filter. Further, the filtrate was passed 10 times through 0.1 μm polycarbonate membrane filter. A 20 mM citrate buffer was added thereto to prepare a liposome suspension containing 50 mg/ml phosphatidylcholine. Separately, 200 mg lactose, 56 mg $Na_2HPO_4.12 H_2O$ and 12 mg hydrous citric acid were added to 10 mg UCN-01, and the mixture was dissolved in distilled water to give 10 ml solution which was then introduced into a glass vial and lyophilized. After lyophilization, the glass vial was returned to normal pressure under a nitrogen stream and sealed to give a lyophilized product of UCN-01 in it. To the lyophilized product was added 2 ml of the previously prepared liposome suspension. A 0.1 ml aliquot was removed from it followed by addition of 0.9 ml of the liposome suspension. Further, 4 ml of 10.4 mM aqueous sodium hydroxide was added thereto and left at 70° C. for 10 minutes so that UCN-01 was encapsulated in liposomes.

EXAMPLE 30

A 0.02 ml of 71 mg/ml PEG-DSPE ethanol solution was added to 2 ml liposome prepared in Example 29 and the mixture was left at 70° C. for 10 minutes whereby the surface was coated with PEG.

EXAMPLE 31

10 ml of 20 mM citrate buffer, pH 4.0 was added to 1 g hydrogenated soybean lecithin and the mixture was shaken and stirred with a Vortex mixer. The suspension was passed 5 times through 0.4 μm polycarbonate membrane filter. Further, the filtrate was passed 10 times through 0.1 μm polycarbonate membrane filter. A 20 mM citrate buffer was added thereto to prepare a liposome suspension containing 60 mg/ml phosphatidylcholine. Separately, 200 mg lactose, 56 mg $Na_2HPO_4.12 H_2O$ and 12 mg hydrous citric acid were added to 10 mg UCN-01, and the mixture was dissolved in distilled water to give 10 ml solution which was then introduced into a glass vial and lyophilized. After lyophilization, the glass vial was returned to normal pressure under a nitrogen stream and sealed to give a lyophilized product of UCN-01 in it. To this lyophilized product was added 2 ml of the previously prepared liposome suspension. A 0.2 ml aliquot was removed from it followed by addition of 1.47 ml of the liposome suspension. Further, 0.33 ml of 200 mM aqueous sodium hydroxide was added thereto and left at 70° C. for 10 minutes so that UCN-01 was encapsulated in liposomes.

EXAMPLE 32

A 0.02 ml of 358 mg/ml PEG-DSPE ethanol solution was added to 2 ml liposome prepared in Example 31 and the mixture was left at 70° C. for 10 minutes whereby the surface was coated with PEG.

Comparative Example 1

200 mg lactose, 56 mg sodium hydrogen phosphate (12 $H_2O$ salt) and 12 mg hydrous citric acid were added to 10 mg UCN-01, and the mixture was dissolved in distilled water to give 10 ml solution which was then introduced into a glass vial and lyophilized. After lyophilization, the glass vial was returned to normal pressure under a nitrogen stream and sealed to give a lyophilized product of UCN-01 in it. 10 ml physiological saline was added to the lyophilized product. A 0.1 ml aliquot was removed from it followed by addition of 0.9 ml physiological saline.

Test Example 5

The UCN-01 encapsulating liposome prepared in Example 28 was ultracentrifuged (110,000×g, 2 hours) at 4° C. UCN-01 before ultracentrifugation and UCN-01 in the supernatant after ultracentrifugation were calculated in the same manner as in Test Example 4.

The results are shown in Table 6.

TABLE 6

| Encapsulation efficiency of UCN-01 | |
|---|---|
| Sample | Encapsulation Efficiency of UCN-01 (%) |
| Example 28 | 100.0 |

Table 6 shows that a liposome preparation with a high encapsulation efficiency of UCN-01 was obtained.

Test Example 6

To determine the leakage of UCN-01 from liposomes in human AGP-added rat plasma (human AGP, 0.5 mg/ml), 0.06 ml of each of UCN-01 encapsulating liposome suspensions prepared in Example 30 and 5.94 ml rat plasma were mixed Mixture I and stored at 37° C. as Mixture I. 3 hours later, 1.5 ml specific gravity solution (a mixture with a specific gravity of 1.244, consisting of 713.09 ml distilled water, 7.891 g NaCl, and 279.07 g NaBr) was added to Mixture I and subjected to ultracentrifugation (110,000×g, 3 hours) at 4° C. UCN-01 Mixture I, and UCN-01 in the upper and lower layers after ultracentrifugation were quantified by high performance liquid chromatography (under the same conditions as in Test Example 4) to determine the change with time of degree of remaining UCN-01 in the liposomes.

The degree of remaining UCN-01 was determined by the following formula:

Degree of remaining UCN-01 (%)=[{(C−A×D/B)×1}/E×1.5]×100

A: Concentration of Compound (I) (mg/ml) in the upper layer after ultracentrifugation after it was added in the free form.

B: Concentration of Compound (I) (mg/ml) in the lower layer after ultracentrifugation after it was added in the free form.

C: Concentration of Compound (I) (mg/ml) in the upper layer after ultracentrifugation after it was added in the form of liposomes.

D: Concentration of Compound (I) (mg/ml) in the lower layer after ultracentrifugation after it was mixed in the form of liposomes.

E: Concentration of Compound (I) (mg/ml) in the Mixture I before ultracentrifugation.

The results are shown in Table 7.

TABLE 7

| Degree of Remaining UCN-01 (%) | |
|---|---|
| Sample | Degree of Remaining UCN-01 (%) |
| Example 30 | 74 |

Test Example 7

To examine the change of UCN-01 encapsulated in liposomes in the plasma of a rat (SD strain rat, male, 8 week-old) administered human AGP, each of the UCN-01 encapsulating liposome suspensions prepared in Example 30 and Comparative Example I was administered at a dosage of 0.35 mg/kg into each rat via the left femoral vein. At each point in time, blood was collected from the jugular vein. And UCN-01 concentration in the plasma was determined. FIG. 1 shows the change of UCN-01 concentration in the plasma of a rat with the elapse of time. 3 hours later, the whole blood was collected through the central vein and fractionated into a liposome fraction (upper layer) and an AGP-bound fraction (low layer) in the same manner as in Test Example 6, and the content of UCN-01 in each fraction was quantified.

The degree of remaining UCN-01 was determined by the following formula:

Degree of Remaining UCN-01 (%)=[A/(A+B)]×100

A: Concentration of Compound (I) (mg/ml) in the upper layer after ultracentrifugation.

B: Concentration of Compound (I) (mg/ml) in the lower layer after ultracentrifugation.

The results are shown in FIG. 1 and Table 8.

TABLE 8

| Degree of Remaining UCN-01 (%) | |
|---|---|
| Sample | Degree of Remaining UCN-01 (%) |
| Example 30 | 91 |

Table 7, FIG. 1, and Table 8 show that liposomes being stable even in the human AGP-added rat plasma were obtained particularly in the case where the surface of the lipid membrane was coated with PEG by the method of Example 30.

Test Example 8

To examine the anti-tumor activity of the UCN-01 encapsulated in liposome, a suspension of each of the UCN-01 encapsulating liposomes prepared in Examples 31 and 32 was administered for every 5 day via the tail vein into a nude mouse having been inoculated subcutaneouslly with human pancreatic cancer PSN-1 cells. The tumor size and body weight at each point in time were determined. The results are shown in Table 9.

TABLE 9

| Anti-Tumor Activity of UCN-01 Liposome | | |
|---|---|---|
| Sample | T/C[a] | Change in Body Weight (g) |
| Example 31 | 0.65 | −1.8 |
| Example 32 | 0.51 | −2.1 |

[a]Tumor size in mice administered the liposome/tumor size in non-treated mice.

Table 9 shows that the liposome preparation of the present invention possessed anti-tumor activity.

INDUSTRIAL APPLICABILITY

According to the present invention, there is provided a liposome preparation in which a medically useful indolocarbazole derivative has been included.

We claim:

1. A liposome preparation comprising an indolocarbazole derivative represented by formula (I):

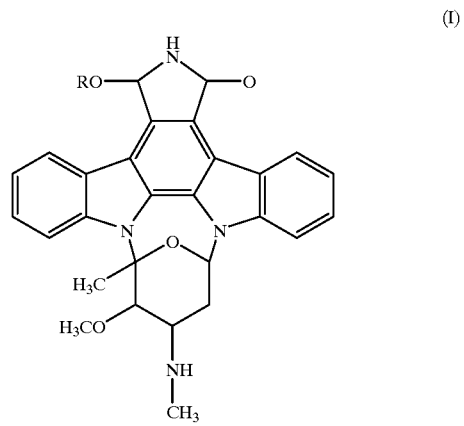

(I)

wherein R represents hydrogen or lower alkyl, said indolocarbazole derivative being encapsulated into a liposome comprising lipids.

2. A liposome preparation according to claim 1 wherein said lipids are phospholipids.

* * * * *

UNITED STATES PATENT AND TRADEMARK OFFICE
CERTIFICATE OF CORRECTION

PATENT NO.   : 6,045,822
DATED        : April 4, 2000
INVENTOR(S)  : Yasuki Kato et al.

It is certified that error appears in the above-identified patent and that said Letters Patent is hereby corrected as shown below:

Title page,
Item [54], In the title, "DESCRIPTION" should be deleted; and

Item [57] ABSTRACT,
Line 1, "inventions" should read -- invention --.

Column 1,
Line 3, "DESCRIPTION" should be deleted;
Line 53, "effectively" should read -- effectively. --; and
Line 55, "thightly" should read tightly --.

Column 2,
Line 67, "phosphatidylgycerol," should read -- phosphatidylglycerol, --.

Column 3,
Line 48, "an" should read -- a --.

Column 4,
Line 2, "Lyoprotectants" should read -- Lyoprotectant --;
Line 14, "OF DESCRIPTION" should read -- DESCRIPTION OF --;
Line 23, "phosphatidylcholine" should read -- Phosphatidylcholine --; and
Line 33, "a" should be deleted.

Column 6,
Line 4, "was" should read -- were --.

Column 8,
Line 34, "sodium" should read -- sodium hydroxide --.

Column 9,
Line 7, "phosphatidylgycerol" should read -- phosphatidylglycerol --"; and
Line 29, "9.0 nM" should read --9.0 mM --.

Column 10,
Line 35, "triethylamine)," should read -- triethylamine). --.

Column 11,
Line 5, "thereto" should read -- thereto to --;
Line 18, "encaspulated" should read -- encapsulated --; and
Line 44, "A" should be deleted.

UNITED STATES PATENT AND TRADEMARK OFFICE
CERTIFICATE OF CORRECTION

PATENT NO. : 6,045,822
DATED : April 4, 2000
INVENTOR(S) : Yasuki Kato et al.

It is certified that error appears in the above-identified patent and that said Letters Patent is hereby corrected as shown below:

Column 12,
Line 6, "A" should be deleted.
Line 47, "Mixture I" (first occurrence) should be deleted.

Column 13,
Line 31, "(low" should read -- (lower --.

Column 14,
Line 4, "taneouslly" should read -- taneously --; and
Line 16, "administered the" should read -- which were administered the --.

Signed and Sealed this

Twenty-second Day of January, 2002

Attest:

Attesting Officer

JAMES E. ROGAN
*Director of the United States Patent and Trademark Office*